United States Patent [19]

Previc et al.

[11] Patent Number: 5,094,954

[45] Date of Patent: Mar. 10, 1992

[54] PRODUCTION OF ENDOSPORES FROM PASTEURIA BY CULTURING WITH EXPLANTED TISSUE FROM NEMATODES

[75] Inventors: Edward P. Previc; Robert J. Cox, both of Gainesville, Fla.

[73] Assignee: University of Florida, Gainesville, Fla.

[21] Appl. No.: 258,275

[22] Filed: Oct. 14, 1988

[51] Int. Cl.$^5$ .......................... C12N 3/00; C12N 1/20
[52] U.S. Cl. ................................. 435/242; 435/252.1; 435/822
[58] Field of Search ...................... 435/822, 240.2, 242, 435/240.21, 243, 240.47, 252.1, 267; 424/93

[56] References Cited

FOREIGN PATENT DOCUMENTS

| | | | |
|---|---|---|---|
| 62-29506 | 2/1987 | Japan . | |
| 1147316 | 3/1985 | U.S.S.R. | 435/260 |
| 8601074 | 2/1986 | World Int. Prop. O. | 424/93 |

OTHER PUBLICATIONS

Sasser, J. N. (1980) "Root-Knot Nematodes: A Global Menace to Crop Production", Plant Disease 64(1):36–41.

Sayre, R. M. (1980) "Promising Organisms for Biocontrol of Nematodes", Plant Disease 64:527–532.

Stirling, G. R. (1984) "Biological Control of *Meloidogyne javanica* with *Bacillus penetrans*", Phytopathology 74:55–60.

Sayre, R. M., M. P. Starr, A. M. Golden, W. P. Wergin, and B. Y. Endo (1988) "Comparison of *Pasteuria penetrans* from *Meloidogyne incognita* with a Related Mycelial and Endospore-Forming Bacterial Parasite from *Pratylenchus brachyrus*", Proc. Helminthol. Soc. Wash. 55(1):28–49.

Starr, M. P., and R. M. Sayre (1988) "*Pasteuria thornei* sp. nov. and *Pasteuria penetrans* sensu stricto emend., Mycelial and Endospore-Forming Bacteria Parasitic, Respectively, on Plant-Parasitic Nematodes of the Genera Pratylenchus and Meloidogyne", Ann. Inst. Pasteur/Microbiol. 139:11–31.

Verdejo, S., and R. Mankau (1986) "Culture of *Pasteuria penetrans* in *Meloidogyne incognita* on Oligoxenic Excised Tomato Root Culture", J. Nematology 18:365.

Reise, R. W., K. J. Hackett, R. M. Sayre, and R. N. Huettel (1988) "Factors Affecting Cultivation of Three Isolates of Pasteuria sp.", Abstracts of the 27th Annual Meeting, Society of Nematologists, p. 75.

Wolf, K., "Cold-Blooded Vertebrate Cell and Tissue Culture", Methods in Enzymology, vol. LVIII, Jacoby and Pastan, Ed., pp. 466–477, 1979.

Stirling, G. et al., "Attachment of *Pasteuria penetrans* spores to the Cuticles of Root-Knot nematodes", Revue Nématol. 9(3): 251–260 (1986).

Starr et al., "*Pasteuria Thornei* sp. nov. and *Pasteuria penetrans* sensu stricto Emend., Mycelial and Endospore-Forming Bacteria Parasitic, Respectively, on Plant-Parasitic Nematodes of the Genera Pratylenchus and Meloidogyne", Ann. Inst. Pasteur/Microbiol. (1988) 139, pp. 11–31.

Bhattacharya et al., "*Pasteuria penetrans*, A Pathogen of the genus Heterodera, its Effect on Nematode Biology and Control", Indian J. Nematol. 18(1): pp. 61–70 (1988).

*Primary Examiner*—Douglas W. Robinson
*Assistant Examiner*—Marian Knode
*Attorney, Agent, or Firm*—Saliwanchik & Saliwanchik

[57] ABSTRACT

Disclosed here is a novel method for producing bacterial endospores which can be used as biocontrol agents for nematodes. Advantageously, the novel method does not require that bacteria be grown on living nematodes. Instead, explanted nematode tissue is used as the growth medium for the bacteria. The invention further concerns novel compositions comprising spores produced using the disclosed process.

5 Claims, No Drawings

PRODUCTION OF ENDOSPORES FROM PASTEURIA BY CULTURING WITH EXPLANTED TISSUE FROM NEMATODES

BACKGROUND OF THE INVENTION

This invention relates to a method for the production of bacterial endospores from Pasteuria, or Pasteuria-like, bacteria. These bacteria are able to produce endospores that have the unique and useful property of being able to attach to, infect, grow in, re-sporulate in, and kill certain types of phytopathogenic nematodes and other soil-dwelling nematodes.

The worldwide destructive capacity of nematodes on cultured plants and the consequent loss of crop productivity are well known (Sasser, J. N. [1980] Plant Disease 64(1):36–41). Chemical nematicides, which have been the control method of choice, are rapidly becoming anathematized because of their real and potential adverse impacts on the environment; the need for development of alternative, bio-rational control agents of nematodes has been widely stated.

Endospore-forming bacteria of the Pasteuria group have been publicly recognized as potential biorational control agents of plant-pathogenic nematodes (Sayre, R. M. [1980] Plant Disease 4:527–532; Stirling, G. R. [1984] Phytopathology 74:55–60). The first report of a Pasteuria-like organism infecting nematodes was by N. A. Cobb (2nd ed. Hawaiian Sugar Planters Assoc., Expt. Sta. Div. Path. Physiol Bull., vol. 5, pp. 163–195, 1906), who observed numerous refractile spores in nematodes of the species *Dorylaimus bulbiferous.* R. M. Sayre et al. (Sayre, R. M., M. P. Starr, A. M. Golde, W. P. Wergin, and B. Y. Endo [1988] Proc. Helminthol. Soc. Wash. 55(1):28–49) suggested that the endospore-forming bacterium *Pasteuria penetrans* is a specific parasite of the root-knot nematode *Meloidogyne incognita* and proposed that other bacteria of the "Pasteuria group" deserve separate species designations. Starr et al. (Starr, M. P., and R. M. Sayre [1988] Ann. Inst. Pasteur/Microbiol. 139:11–31) assigned the species name *Pasteuria thornei* sp. nov. to the endospore-forming bacterium that is primarily parasitic on the root-lesion nematode *Pratylenchus brachyurus,* and the species name *Pasteuria penetrans sensu stricto* emend. to the endospore-forming bacterium which is primarily parasitic on the rootknot nematode *Meloidogyne incognita.*

Although bacteria of the Pasteuria group have a recognized potential for use as biorational control agents against phytopathogenic nematodes, their widespread use in commercial agriculture will depend on the availability of reliable methods for the large-scale production of spores having specificity against the phytopathogenic nematodes of concern to farmers. One method of production would be to induce spore formation following true in vitro, axenic growth of the vegetative phase of any select Pasteuria species on an artificial growth medium consisting of inexpensive, readily available materials. Such systems are not known at this time.

Most of the experimental work with the Pasteuria group of bacteria has used spores produced in live nematodes, cultivated on whole plants in greenhouses where aseptic conditions do not prevail. In two exceptions, Verdeho et al. (Verdeho, S., and R. Mankau [1986] *Journal of Nematology* 18:635) have reported on the oligoxenic culture of *Pasteuria penetrans* in live *Meloidogyne incognita* on excised tomato root culture; and Reise et al. (Reise, R. W., K. J. Hackett, R. M. Sayre, and R. N. Huettel [1988] Abstracts of the 27th Annual Meeting Society of Nematologists, p. 75) have studied factors in various tissue culture media affecting Pasteuria isolates from *Heterodera glycines, Meloidogyne incognita,* and *Pratylenchus brachyurus.* Their attempts are directed at a genuine in vitro cultivation of Pasteuria, which attempts fail on the basis of the fundamental criterion that a genuine in vitro cultivation of any prokaryotic organism must be marked by a continual survival and proliferation of the organisms, upon transfer to a fresh medium, at some definable growth rate that is characteristic of the genotype of the organism and the environmental conditions.

Our invention does not rely on the genuine in vitro cultivation of the Pasteuria, but is directed at the production of Pasteuria spores on explanted or cultured nematode tissue. The key difference is that our chosen medium is nematode tissue, from a natural host or alternative host nematode, whose capacity to support Pasteuria growth and subsequent sporulation we have experimentally demonstrated.

More particularly, this invention relates to the production of endospores from the post-vegetative phases of *Pasteuria penetrans, Pasteuria thornei,* and related Pasteuria-like organisms which have been grown vegetatively on any of a variety of growth substrates consisting of explanted nematode tissues or nematode cell cultures, but in the absence of whole living phytopathogenic nematodes and their usual plant host materials.

BRIEF SUMMARY OF THE INVENTION

The subject invention is a novel means for growing endospores useful in the biological control of nematodes. According to the subject invention, Pasteuria spores, such as those that infect the root-lesion nematode *Pratylenchus brachyurus* or other specified host nematodes, are first attached to juveniles and adults of *Pratylenchus brachyurus* or other specified nematode. The nematodes with attached spores are then decapitated and decaudated. The viable remaining tissues of the nematode cadaver is then explanted into various standard and modified tissue culture media. Advantageously, this explanted nematode tissue supports growth of bacterial mass and an increase in the number of cellular units of the vegetative stage of the infecting Pasteuria bacteria. Subsequently, sporulation occurs from the late vegetative phase of the Pasteuria with production of mature, dormant spores that are infective for the original host nematode, *Pratylenchus brachyurus,* or other nematode species.

DETAILED DESCRIPTION OF THE INVENTION

The subject invention is a novel method for growing Pasteuria bacteria for the production of spores which can then be used as a biocontrol agent for certain nematodes. In particular, the novel procedure involves growing the bacteria on the explanted nematode tissue. The tissue may be prepared, for example, by decapitating and decaudating nematodes, or by osmotic and/or enzymatic disruption of the nematode cuticle.

The nematode tissue is explanted onto media which is designed to nourish the tissue and keep it in a metabolically active state. The tissue is then induced into growth and cell proliferation. This can be done, for example, by treating the tissue with growth hormones, mitogenic agents, and/or oncogenic viruses such as Epstein-Barr virus.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of Nematodes

Greenhouse populations of *Pratylenchus brachyurus* nematodes, both uninfected and infected with *Pasteuria thornei*, were raised on seedlings of 5098 Iochief hybrid sweet corn (Park Seed Company, Greenwood, S.C.). Monoxenic cultures of *Pasteuria thornei* were raised on excised corn roots on Gamborg's B-5 plant cell medium (Gibco Laboratories, Chagrin Falls, Ohio). Soil from IFAS (Green Acres Farm, Alachua County, Fla.) was the source of Pasteuria-infected and unifected *P. brachyurus*. Soil and corn roots were processed by standard methods to recover adult and juvenile nematodes. Only live, active nematodes obviously free of advanced Pasteuria infections were selected for further experimentation.

In a representative sample of test nematodes, 19 of 80 (24%) had one or more attached Pasteuria spores, examined at 1250× in a phase microscope. Nematodes from this population were washed once in sterile water and transferred to a solution of 1 part sterile water plus 2 parts Sigma catalog no. A9909 antibiotic/antimycotic solution containing 25 $\mu$g/ml amphotericin, 10,000 units/ml penicillin, and 10 mg/ml streptomycin, all in 0.9% NaCl.

Nematodes were incubated in antibiotic/antimycotic solution in the dark for 1 hr at 23° C. Heads and tails were severed from individual nematodes using a microdissection scalpel. The remaining carcass of each nematode was placed in a well of a 24-well plastic tissue culture plate (Corning catalog no. 25820) with 0.5 ml of a modified "Hirumi-Maramorosch" medium, described below. When all wells were filled, each plate was covered with a lid, sealed with sterile Parafilm, placed in a Zip-lock bag, and incubated in the dark at 23° C.

EXAMPLE 2

Medium

The medium into which nematode tissues were explanted was based on that described by Hirumi et al. (Hirumi, J., and K. Maramorosch [1967] 2nd International Colloquium on Invertebrate Tissue Culture, Instituto Lombardo Fondazione Baselli pp. 203–217). Among other components, these media incorporated medium M199 of Morgan et al. ([1950] Proc. Soc. Exp. Biol. Med. 73:1). M199 used in the present example came from Gibco Laboratories (catalog no. 320-1150AG), and the stock salt solution of Hirumi and Maramorosch was replaced by Earle's balanced salt solution supplemented with lactalbumin hydrolyzate (1 g/100 ml), fructose (0.04 g/100 ml), and sucrose (0.04 g/100 ml). (Gibco Laboratories catalog no. 310-4010AG).

EXAMPLE 3

Explanted *Pratylenchus brachyurus* tissues prepared as above were examined after 17 days incubation, at which time 6 out of 22 tissue explants contained mature Pasteuria spores. Additional explants were examined at 24 days and 4 out of 40 were found to have spores.

Direct microscopic counts of spores in the explanted tissue gave estimates of 200-plus spores per each infected nematode carcass.

EXAMPLE 4

The procedure of Example 1 was used to practice the invention on a separate batch of *Pratylenchus brachyurus* in which *Pasteuria thornei* spores were found to be attached to 18 of 132 (12%) of the recovered nematodes. Explanted *Pratylenchus brachyurus* tissues prepared from this population of nematodes were first examined after 18 days incubation at which time 1 out of 20 tissue explants contained mature Pasteuria spores. Additional explants were examined at 40 days, at which time over 25% (6 out of 20) contained developing spores and/or vegetative growth of Pasteuria.

EXAMPLE 5

Greenhouse populations of *Meloidogyne incognita* nematodes, both uninfected and infected with *Pasteuria penetrans*, were raised on Rutgers PS tomato seedlings (Seminole Stores, Gainesville, Fla). Various races of uninfected *Meloidogyne incognita* were obtained from the Fort Lauderdale Research and Education Center of IFAS. Soil and tomato roots were processed by standard methods to recover adult and juvenile nematodes and nematode eggs. Surface-sterilized eggs were used to start monoxenic cultures of *Meloidogyne incognita*, which were then raised on excised tomato roots on Gamborg's B-5 plant cell medium.

Spores of *Pasteuria penetrans* contained in crude powders made from tomato roots infested with infected nematodes were provided by Grover Smart, IFAS Department of Nematology and Entomology, Gainesville, Fla, and are henceforth referred to as "spore powder." The actual content of mature, dormant spores in this powder could not be determined, but was probably in excess of 10,000 spores per mg. Several egg masses from *Meloidogyne incognita* race 3 SEMA were incubated for 72 hours in the dark at 23° C. in an aqueous suspension consisting of spore powder (10 mg/ml) and nystatin (10,000 units/ml). Of the emerging Meloidogyne juveniles sampled, 13 of 58 (29%) were found to have Pasteuria spores attached to their cuticles. Several individual juveniles were collected, decapitated, decaudated, and transferred to modified Hirumi-Maramorosch tissue culture medium as with Pratylenchus nematodes cf Example 1.

After incubation for 23 days in the dark at 23° C., 2/26 Meloidogyne tissue explants examined contained developing Pasteuria in the vegetative and pre-spore stages. At 59 days, mature spores were observed on cultured *M. incognita* tissues.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A process for producing endospores from Pasteuria, said process comprising growing Pasteuria bacteria on tissue removed from either *Pratylenchus brachyurus* nematodes or *Meloidogyne incognita* nematodes, said process comprising the steps of (a) removing tissue having Pasteuria spores from either living or newly killed *Pratylenchus brachyurus* or *Meloidogyne incognita* nematodes such that viable tissue is obtained;
(b) explanting said viable tissue into tissue culture medium capable of supporting the growth of said viable tissue; and
(c) allowing said tissue and bacteria to grow until sporulation of said Pasteuria occurs.

2. The process, according to claim 1, wherein said viable tissue is removed from said nematode by either decapitating and decaudating said nematode or by osmotic or enzymatic disruption of the cuticle of said nematode.

3. The process, according to claim 1, wherein said nematode is a *Pratylenchus branchyurus*.

4. The process, according to claim 1, wherein said nematode is a *Meloidogyne incognita*.

5. The process, according to claim 1, wherein said bacteria are *Pasteuria thornei*.

* * * * *

UNITED STATES PATENT AND TRADEMARK OFFICE
CERTIFICATE OF CORRECTION

PATENT NO. : 5,094,954
DATED : March 10, 1992
INVENTOR(S) : Edward P. Previc It is certified that error appears in the above-identified patent and that said Letters Patent is hereby corrected as shown below:

Column 1, line 27: "Plant Disease 4:527" should read --Plant Disease 64:527--.

Column 2, line 1: "Abstracts of the 27th Annual Meeting Society of Nematologists" should read --Abstracts of the 27th Annual Meeting, Society of Nematologists--.

Column 4, line 15: "after 18 days incubation at which time" should read --after 18 days incubation, at which time--.

Column 6, line 6: "*Pratylenchus branchyurus*" should read --*Pratylenchus brachyurus*--.

Signed and Sealed this

First Day of June, 1993

Attest:

MICHAEL K. KIRK

*Attesting Officer*  Acting Commissioner of Patents and Trademarks